(12) United States Patent
Herman et al.

(10) Patent No.: US 6,350,463 B1
(45) Date of Patent: Feb. 26, 2002

(54) METHOD OF TREATMENT FOR PREMATURE RUPTURE OF MEMBRANES IN PREGNANCY (PROM)

(75) Inventors: Stephen J. Herman, Andover, MA (US); Glenn M. Kazo, New Ipswich, NH (US); David J. Enscore, Sudbury; J. Jeffrey Kablik, Tyngsboro, both of MA (US)

(73) Assignee: Andre Bieniarz, Chicago, IL (US)

( * ) Notice: Subject to any disclaimer, the term of this patent is extended or adjusted under 35 U.S.C. 154(b) by 0 days.

(21) Appl. No.: 09/316,879

(22) Filed: May 21, 1999

Related U.S. Application Data

(60) Provisional application No. 60/086,624, filed on May 23, 1998.

(51) Int. Cl.⁷ .................................................. A61F 2/02
(52) U.S. Cl. ....................................... 424/425; 424/424
(58) Field of Search .................................. 424/424, 425

(56) References Cited

U.S. PATENT DOCUMENTS

| | | | |
|---|---|---|---|
| 4,007,249 A | 2/1977 | Erb | 264/222 |
| 4,100,923 A | 7/1978 | Southern | 128/348 |
| 4,128,100 A | 12/1978 | Wendorff | 128/335.5 |
| 4,188,951 A | 2/1980 | Higuchi et al. | 128/260 |
| 4,693,704 A | 9/1987 | Ogita | 604/55 |
| 4,722,730 A | 2/1988 | Levy et al. | 604/118 |
| 5,201,745 A | 4/1993 | Tayot et al. | 606/151 |
| 5,283,063 A | 2/1994 | Freeman | 424/427 |
| 5,338,297 A | 8/1994 | Kocur et al. | 604/96 |
| 5,410,016 A | 4/1995 | Hubbell et al. | 528/354 |
| 5,469,867 A | 11/1995 | Schmitt | 128/898 |
| 5,516,532 A | 5/1996 | Atala et al. | 424/548 |
| 5,573,934 A | 11/1996 | Hubbell et al. | 435/177 |

(List continued on next page.)

FOREIGN PATENT DOCUMENTS

WO 96/28539 9/1996

OTHER PUBLICATIONS

Akala, E.O. et al., "Novel pH–sensitive hydrogels with adjustable swelling kinetics," *Biomaterials*, 19:1037–1047 (1998).

Alleyne et al., "Efficacy and biocompatibility of a photopolymerized, synthetic, absorbable hydrogel as a dural sealant in a canine craniotomy model," *J. Neurosurg.*, 88:308–313 (1998).

Andreopoulos et al., "Release of Drugs from Polymeric Hydrogels," *J. Biomater. Appls.*, 12:291–99 (1998).

Anseth et al., "Mechanical properties of hydrogels and their experimental determination," *Biomaterials*, 17:1647–57 (1996).

Blanco et al., "Slow releasing of ara–C from poly(2–hydroxyethyl methacrylate) and poly(2–hydroxyethyl methacrylate–co–N–vinyl–2–pyrrolidone) hydrogels implanted subcutaneously in the back of rats," *Biomaterials*, 19:861–69 (1998).

(List continued on next page.)

*Primary Examiner*—Carlos Azpuru
(74) *Attorney, Agent, or Firm*—Marshall, Gerstein, & Borun

(57) ABSTRACT

Premature Rupture of the Membranes (PROM) is a serious complication of pregnancy. PROM is treated by creation of a seal or barrier at the site of the rupture or in or near the cervix, thereby controlling the loss of amniotic fluid and preventing bacterial access. Instruments and techniques for application of sealing and barrier-forming materials at appropriate sites are described, as well as appropriate selection of materials and formation techniques. The instruments and techniques facilitate application of any fluent material to physiology associated with pregnancy and rendering the fluent material non fluent so as to form a barrier of seal.

38 Claims, 1 Drawing Sheet

U.S. PATENT DOCUMENTS

| | | | | |
|---|---|---|---|---|
| 5,575,815 A | 11/1996 | Slepian et al. | ................. | 623/1 |
| 5,583,114 A | 12/1996 | Barrows et al. | ............... | 514/21 |
| 5,612,050 A | 3/1997 | Rowe et al. | ................ | 424/423 |
| 5,662,609 A | 9/1997 | Slepian | ........................ | 604/101 |
| 5,665,477 A | 9/1997 | Meathrel et al. | ............ | 428/500 |
| 5,674,192 A | 10/1997 | Sahatjian et al. | ............. | 604/28 |
| 5,698,189 A | 12/1997 | Rowe et al. | ............. | 424/78.08 |
| 5,714,159 A | 2/1998 | Shalaby | ..................... | 424/426 |
| 5,749,915 A | 5/1998 | Slepian | .......................... | 623/1 |
| 5,749,968 A | 5/1998 | Melanson et al. | .......... | 118/300 |
| 5,752,974 A | 5/1998 | Rhee | .......................... | 606/214 |
| 5,769,091 A | 6/1998 | Simon et al. | ............... | 128/885 |
| 5,779,673 A | 7/1998 | Roth et al. | ................... | 604/101 |
| 5,800,373 A | 9/1998 | Melanson et al. | ............ | 602/52 |
| 5,810,721 A | 9/1998 | Mueller et al. | ............... | 600/200 |
| 5,844,016 A | 12/1998 | Sawhney et al. | ............. | 522/22 |
| 5,849,035 A | 12/1998 | Pathak et al. | .................. | 623/1 |
| 5,855,619 A | 1/1999 | Caplan et al. | ................ | 623/11 |
| 5,863,551 A | 1/1999 | Woerly | ....................... | 424/423 |
| 5,879,713 A | 3/1999 | Roth et al. | .................. | 424/489 |
| 5,900,245 A | 5/1999 | Sawhney et al. | ........... | 424/426 |
| 5,993,856 A | 11/1999 | Ragavan et al. | ............ | 424/489 |

OTHER PUBLICATIONS

Blue et al., "In Vivo Results of Hydrogel Composite Pericardial Substitutes," *ASAIO Transactions*, 37:M152–53 (1991).

Chetoni et al., "Silicone rubber/hydrogel composite ophthalmic inserts: preparation and preliminary in vitro/in vivo evaluation," *Eur. J. Pharm. Biopharm.*, 46:125–32 (1998).

Cífková et al., "Silicone rubber–hyrogel composites as polymeric biomaterials," *Biomaterials*, 11:393–396 (1990).

Corkhill et al., "Synthetic hydrogels VI. Hydrogel composites as wound dressings and implant materials," *Biomaterials*, 10:3–10 (1989).

Draye et al., "In vitro release characteristics of bioactive molecules from dextran dialdehyde cross–linked gelatin hydrogel films," *Biomaterials*, 19:99–107 (1998).

Gomez et al., "Poly(acrylamide–co–monoethyl Itaconate) Hydrogels as Devices for Cytarabine Release in Rats," *J. Pharm. Pharmacol.* 50:703–712 (1998).

Hoffman, "'Intelligent' Polymers in Medicine and Biotechnology," *Artificial Organs*, 19(5):458–467 (1995).

Hong et al., "Comparison of bone regeneration in a rabbit skull defect by recombinant human BMP–2 incorporated in biodegradable hydrogel and in solution," *J. Biomater. Sci. Polym. Ed.*, 9(9):1001–1014 (1998).

Horák et al., "Hydrogels in endovascular embolization," *Biomaterials*, 9:367–371 (1988).

Iza et al., "Hydrogels of poly(ethylene glycol): mechanical characterization and release of a model drug," *J. Controlled Release*, 52:41–51 (1998).

Kikkinides et al., "A two–phase model for controlled drug release from biphasic polymer hydrogels," *J. Controlled Release*, 51:313–325 (1998).

Lopour et al., "Silicone rubber–hydrogel composites as polymeric biomaterials," *Biomaterials*, 11:397–402 (1990).

Martin et al., "Highly swelling hydrogels from ordered galactose–based polyacrylates," *Biomaterials*, 19:69–76 (1998).

Merrill et al., Partitioning and diffusion of solutes in hydrogels of poly(ethylene oxide) *Biomaterials*, 14(15):1117–26 (1993).

Nakayama et al., "Surface Fixation of Hydrogels Heparin and Glucose Oxidase Hydrogelated Surfaces," *ASAIO Journal*, 38:M421–24 (1992).

Oxley et al., "Macroporous hydrogels for biomedical applications: methodology and morphology," *Biomaterials*, 14:1064–72 (1993).

Ranger et al., "Pneumostasis of Experimental Air Links with a New Photopolymerized Synthetic Tissue Sealant," *Am. Surg.*, 63(9):788–795 (Sep., 1997).

Slepian et al., "Polymeric Endoluminal Gel Paving: Therapeutic Hydrogel Barriers and Sustained Drug Delivery Depots for Local Arterial Wall Biomanipulation," *Semin. Intervent. Cardiol.*, 1:103–16 (1996).

Slepian, "Polymeric Endoluminal Paving and Sealing: Therapeutic at the Crossroad of Biomechanics and Pharmacology," Section IV, Chapter 32, pp. 647–670.

Suggs et al., "Preparation and characterization of poly(propylene fumarate–co–ethylene glycol) hydrogels," *J. Biomater. Sci. Polym. Edn.*, 9(7):653–66 (1998).

Tabata et al., "Bone regeneration by basic fibroblast growth factor complexed with biodegradable hydrogels," *Biomaterials*, 19:807–815 (1998).

Tay et al., "Activity toward thrombin–antithrombin of heparin immobilized on two hydrogels," *Biomaterials*, 10:11–15 (1989).

Trigo et al., "Anticancer drug, ara–C, release from pHEMA hydrogels," *Biomaterials*, 15(14):1181–86 (1994).

Watler et al., "Water content and compression modulus of some heparin–PVA hydrogels," *Biomaterials*, 9:150–54 (1988).

Yamamoto et al., "Ectopic bone formation induced by biodegradable hydrogels incorporating bone morphogenetic protein," *J. Biomater. Sci. Polymer Edn.*, 9(5):439–458 (1998).

Allen and Jones, "Medical Complications of Prematurity," Obstetrics and Gynecology, vol. 67, No. 3, (3/86), pp. 427–437.

Baumgarten and Moser, "The Technique of Fibrin Adhesion for Premature Rupture of the Membranes During Pregnancy," J. Perinat. Med.; 14 (1986), pp. 43–49.

Bonnett et al., "Effect of Endoscopic Light on Developing Rat Retina," Fetal Diagnosis and Therapy, No. 12, pp. 76–80 (1997).

Evans et al., "Fetal Muscle Biopsy: Collaborative Experience with Varied Indications," Obstetrics and Gynecology, vol. 84, No. 6, pp. 913–917, (12/94).

Evans et al., "Endoscopically Assisted Ultrasound—Guided Fetal Muscle Biopsy," Fetal–Diagnosis and Therapy, No. 10, 167–172, (1995).

Gibbs and Blanco, "Premature Rupture of the Membranes," Obstetrics and Gynecology, vol. 60, No. 6, pp. 671–679, (Dec. 1982).

Gunn et al., "Premature Rupture of the Fetal Membranes," Amer. J. Obstet. Gynec., vol. 106, No. 3, pp. 469–483, (Feb. 1, 1970).

Harriman, "Tenacity and Glue Save Pregnancy," Copyright 1997, The New Journal Co.

Johnson et al., "Premature Rupture of the Membranes and Prolonged Latency," Obstetrics and Gynecology, vol. 57, No. 5, pp. 547–556, (May 1981).

Lewis et al. "Effects of Digital Vaginal Examinations on Latency Period in Pretern Rupture of Membranes," Obstetrics and Gynecology, vol. 80, No. 4, pp. 630–634, (Oct. 1992).

Louis–Sylvestre et al., "In Vitro Studies of the Interactions Between Platlets and Amniotic Membranes; A Potential Treatment for Pretern Premature Rupture of the Membranes," Am. J. Obstet. Gynecol, vol. 178, No. 2, pp. 287–293, (Feb. 1998).

Maxwell, "Pretern Premature Rupture of Membranes," Obstetrical and Gyncological Survey, vol. 48, No. 10, pp. 576–583, Copyright © 1993 by Williams & Wilkins.

Ogita et al., "Premature Rupture of the Membranes Managed With a New Cervical Catheter," The Lancet, p. 1330, (Jun. 16, 1984).

Ogita et al., "Transcervical Amnioinfusion of Antibiotics: A Study for Managing Premature Rupture of Membranes," Am. J. Obstet. Gynecol., vol. 158, No. 1, pp. 23–27, (Jan. 1998).

Ogita et al., "Clinical Effectiveness of a New Cervical Indwelling Catheter in the Management of Premature Rupture of the Membranes: A Japanese Collaborative Study," Am. J. Obstet. Gynecol., vol. 159, No. 2, pp. 336–341, (Aug. 1988).

Parry and Strauss III, "Premature Rupture of the Fetal Membranes," New England Journal of Medicine, vol. 338, No. 10, pp. 663–670, (Mar. 5, 1998).

Quintero et al., "In–utero Percutaneous Cytoscopy in the Management of Fetal Lower Obstructive Uropathy," The Lancet, vol. 346, pp. 537–540, (Aug. 26, 1995).

Quintero et al., "Hydrolaparoscopy in the Rabbit: A Fine Model for the Development of Operative Fetoscopy," Am. J. Obstet. Gynecol, vol. 171, No. 4, pp. 1139–1142, (Oct. 1994).

Quintero et al., "Percutaneous Fetal Cytoscopy and Endoscopic Fulguration of Posterior Urethral Valves," Am. J. Obstet. Gynecol., vol. 172, No. 1, Part 1, pp. 206–209, (Jan. 1995).

Quintero et al., "Repair Kinetics of Amnion Cells After Microsurgical Injury," Fetal Diagn. Ther., No. 11, pp. 348–356, (1996).

Quintero et al., "Effect of Endoscopic White Light on the Developing Visual Pathways A Histologic, Histochemical, and Behavioral Study," Am. J. Obstet. Gynecol., vol. 171, No. 4, pp. 1142–1148, (Oct. 1994).

Rubén et al., "Embryoscopy and Fetoscopy, Prenatal Diagnosis: Present and Future Perspectives," vol. 20, No. 3, pp. 563–581, (Sep. 1993).

Taylor and Garite, "Premature Rupture of Membranes Before Fetal Viability," Obstetrics & Gynecology, vol. 64, No. 5, pp. 615–620, (Nov. 1984).

Uchide et al., "Intracervical Fibrin Instillation as an Adjuvant to Treatment for Second Trimester Rupture of Membranes," Arch. Gynecol. Obstet., vol. 255, pp. 95–98, (1994).

Harmanli, et al., "Efficacy of Fibrin Glue for in Vitro Sealing of Human Chorioamniotic Membranes" The Journal of Reproductive Medicine, Inc. vol. 43, No. 11/Nov. 1998 pp. 986–990.

Vergamo et al., "Amnioinfusion for Prevention of Pulmonary Hypoplasia in Second–Trimester Rupture of Pulmonary Hypoplasia in Second–Trimester Rupture of Membranes," American Journal of Perinatology, vol. 14, No. 6, pp. 325–329, Jul. 1997.

METHOD OF TREATMENT FOR PREMATURE RUPTURE OF MEMBRANES IN PREGNANCY (PROM)

RELATED APPLICATIONS

This non-provisional application is a continuation-in-part of and claims the benefit under Title 35, U.S.C. §119(e) of co-pending U.S. provisional application serial No. 60/086,624, filed May 23, 1998, entitled "Method of Treatment for Premature Rupture of Membranes in Pregnancy (PROM)" by Glenn Kazo et al., incorporated herein by reference.

BACKGROUND OF THE INVENTION

PROM, or Premature Rupture Of the Membranes surrounding the fetus (sometimes called the amniotic membrane (AM)) is a serious complication of mid to late pregnancy. PROM, and subsequent leakage of amniotic fluid, is a major precursor of premature delivery, and of concurrent infection. Prematurity and infection are in turn major causes of morbidity and mortality, and frequently lead to permanent impairment of the fetus, as well as high levels of medical expense both prepartum and postpartum.

PROM from any cause is considered here. Known causes of PROM include trauma, surgical intervention, and amniocentesis. However, PROM is primarily "spontaneous", i.e., of unknown origin. It is believed that spontaneous PROM occurs most commonly near the proximal cervix, which is the locus of the highest hydrostatic pressure on the membranes, and is also the most exposed to bacterial attack. However, in most clinical cases the exact location of the rupture in spontaneous or trauma-caused PROM is not known. Such ruptures rarely self-seal.

If membrane rupture could be repaired, or if leakage of amniotic fluid could be minimized or prevented, it is believed that premature delivery could be significantly delayed, thereby significantly extending the degree of fetal maturity. Every day of extension of pregnancy can decrease the severity of fetal impairment due to prematurity by up to one percent; thus, maximizing the duration of pregnancy is clinically important. Cessation of leakage would also tend to minimize intrauterine infection. However, there are at present no reliable techniques for such treatment. In particular, the amniotic membrane is poorly vascularized and slow to heal, and is not easily accessible. Moreover, the location of the rupture is often difficult to determine.

The literature describes attempts to block amniotic fluid release by means of balloons, or with fibrin glue. Neither of these techniques has been sufficiently successful to enter general practice. Restriction of amniotic fluid loss with a balloon or similar device may be ineffective to prevent infection, and fibrin glue is typically rapidly degraded.

Materials and techniques for treating body tissues and sealing leaking lesions in tissues are known.

U.S. Pat. No. 5,410,016 (Hubbell, et al.) describes hydrogels of polymerized and crosslinked macromers comprising hydrophilic oligomers having biodegradable monomeric or oligomeric extensions. Biodegradation occurs at the linkages within the extension oligomers and results in fragments which are non-toxic and easily removed from the body. Applications for the hydrogels include adhering or sealing tissues together.

U.S. Pat. No. 5,575,815 (Slepian, et al.) describes a method for providing a synthetic barrier made of biocompatible polymeric material in vivo which involves application of a material to a tissue or cellular surface such as the interior surface of a blood vessel, tissue lumen or other hollow space. The polymeric material may also be applied to tissue contacting surfaces of implantable medical devices.

U.S. Pat. No. 5,612,050 (Rowe, et al.) describes an apparatus and method for applying an initially fluent material to a surface of a mammalian tissue including soft, living tissue and then activating the material by exposure to an energy source. The device and associated methods enable treatment of medical conditions including the application of a barrier to soft tissue to prevent post-surgical adhesions.

U.S. Pat. No. 5,800,373 (Melanson, et al.) describes a barrier or drug delivery system that is adherent to the surface to which it is applied. Tissue can be stained with a photoinitiator, then a polymer solution or gel having added thereto a defined amount of the same or a different photoinitiator can be applied to the tissue. Exposure of light causes polymerization at the surface, providing adherence and forming a gel. The resulting polymerizable barrier materials are useful for sealing tissue surfaces and junctions against leaks of fluids.

U.S. Pat. No. 5,900,245 (Sawhney, et al.) describes a barrier or drug delivery system which is adherent to the surface to which it is applied. The tissue sealant is capable of conforming to the three dimensional structure of a tissue surface as the tissue bends and deforms during healing processes.

Materials and techniques to treat Premature Rupture Of the Membranes (PROM) during pregnancy are also known.

Baumgarten and Moser, "The Technique of Fibrin Adhesion for Premature Rupture of the Membranes During Pregnancy," J. Perint. Med., 14:43–49 (1986), describe a technique of fibrin adhesion for premature rupture of membranes during pregnancy. Cerclage of the cervix is suggested prior to applying the sealant in order to prevent the fibrin clot from being flushed out prematurely by flow of amniotic fluid, as direct adhesion of the fibrin sealant to the cervical wall is not to be expected.

Uchide et al., "Intracervical Fibrin Installation as an Adjuvant to Treatment for Second Trimester Rupture of Membranes," Arch. Gynecol. Obstet., 255:95–98 (1994), describe the treatment of PROM with cerclage and repeated intercervical applications of fibrin which maintain effectiveness for approximately two weeks. Leakage of amniotic fluid was not completely stopped.

Ogita et al., "Clinical Effectiveness of a New Cervical Indwelling Catheter in the management of Premature Rupture of the Membranes: A Japanese Collaborative Study," Am. J. Obstet. Gynecol., Vol 159, No. 2, pp336–341, (August 1988), describe the use of a cervical catheter which is fixed in the cervical canal by inflating balloons. Patients were assigned bed rest and saline and other fluids were administered daily. The delay in delivery ranged between 3 days and 2.5 weeks.

As the above references indicate, a need exists for improved methods to treat physiological conditions of pregnancy. In particular, improved methods are needed which allow the installation of a barrier serving as a partial or, preferably, complete, hydraulic seal to contain the amniotic fluid within the uterine cavity. This may be achieved by a sealing of the rupture itself, or by a sealing of the cervix to maintain the amniotic fluid in the uterus and therefore largely within the space defined by the amniotic membranes.

SUMMARY OF THE INVENTION

The present invention provides a series of techniques for conversion of fluent to non-fluent material at surfaces of physiology associated with pregnancy.

One aspect of the invention involves a method for treatment of premature rupture of the membranes of pregnancy (PROM), involving applying a fluent material to a tissue selected from at least one of an amniotic membrane, a cervix and a uterine wall, and causing the fluent material to become a non-fluent material, thereby providing an essentially complete seal which retains amniotic fluid.

In another aspect, the invention provides a device for treatment of PROM, wherein the device comprises a proximal end for manipulation of the device, a distal end for insertion into the patient's body, and at least one lumen with an opening at the distal end of the device suitable for delivery of a fluent material to a treatment space bounded by at least one of the uterine wall, the membranes, and the proximal cervix, whereby an at least partial hydraulic seal is created in the vicinity of said space.

In another aspect, the invention involves use of a fluent material for the manufacture of a medicament for use in a method of providing therapeutic treatment to an amniotic membrane of a patient or a uterine wall or cervix of a pregnant patient, the method comprising applying the fluent material to the amniotic membrane of the patient or the uterine wall or cervix of the pregnant patient, and causing the fluent material to become non fluent.

In another aspect, the invention involves use of a fluent material for the manufacture of a medicament for use in a method of treating an amniotic membrane of a patient or a uterine wall or cervix of a pregnant patient by applying the fluent material to the amniotic membrane of the patient or the uterine wall or cervix of the pregnant patient, and causing the fluent material to become non fluent, thereby providing an essentially complete seal which retains amniotic fluid.

In another aspect, the invention involves use of a fluent material for the manufacture of a medicament for use in a method of treating at least one of the cervix, uterine wall, and amniotic membrane of a patient by accessing at least one of the cervix, uterine wall, and amniotic membrane surgically, applying a fluent material to at least one of the cervix, uterine wall and amniotic membrane, and causing the fluent material to become non fluent.

In another aspect, the invention involves use of a fluent material for the manufacture of a medicament for use in a method of treating at least one of a cervix, uterine wall and amniotic membrane of a patient by introducing a treatment device into a vagina of a patient. applying at least one of a synthetic fluent material and synthetic fluent hydrogel to at least one of a cervix, uterine wall and amniotic membrane, and causing at least one of the synthetic fluent material and synthetic fluent hydrogel to become non fluent to form a seal.

In another aspect, the invention involves use of a fluent material for the manufacture of a medicament for use in a method of treating the cervix of a patient by inserting an at least preformed plug comprising at least one of a biologically compatible polymer and a hydrogel into the cervix of a patient to form a seal.

In another aspect, the invention involves use of a fluent material for the manufacture of a medicament for use in a method of treating a treatment site of a uterine wall, amniotic membrane, or cervix of a patient percutaneously by accessing a treatment site of a uterine wall, amniotic membrane, or cervix of a patient percutaneously, and therapeutically treating the treatment site.

In another aspect, the invention involves use of a gelling material for the manufacture of a medicament for use in a method of treating premature rupture of the membranes of pregnancy (PROM) by instilling a gelling material to form a layer in a treatment space, wherein the treatment space is bounded by one or more of the amniotic membrane, the cervix and the uterine wall, and causing the material to form a hydrogel, thereby providing a hydraulic seal which retains amniotic fluid.

In another aspect, the invention involves a method including accessing at least one of the cervix, uterine wall, and amniotic membrane surgically, applying a fluent material to at least one of the cervix, uterine wall and amniotic membrane, and causing the fluent material to become non fluent.

In another aspect, the invention involves a method including introducing a treatment device into a vagina of a patient, applying at least one of a synthetic fluent material and synthetic fluent hydrogel to at least one of a cervix, uterine wall and amniotic membrane, and causing at least one of the synthetic fluent material and synthetic fluent hydrogel to become non fluent to form a seal.

In another aspect, the invention involves a method including inserting at least one of a preformed plug comprising at least one of a biologically compatible polymer and hydrogel into the cervix of a patient to form a seal.

In another aspect, the invention involves a method including inserting at least one of a sheath and tube into a vagina of a patient and placing a treatment device in at least one of the sheath and tube.

In another aspect, the invention involves a method including accessing a treatment site of a uterine wall, amniotic membrane, or cervix of a patient percutaneously, and therapeutically treating the treatment site.

In another aspect, the invention involves a method for treatment of premature rupture of the membranes of pregnancy (PROM), the method including instilling a gelling material to form a layer in a treatment space, wherein the treatment space is bounded by one or more of the amniotic membrane, the cervix and the uterine wall, and causing the material to form a hydrogel, thereby providing a hydraulic seal which retains amniotic fluid.

In another aspect the invention involves a device for treatment of PROM, wherein the device comprises a proximal end for manipulation of the device, a distal end for insertion into the patient's body, and at least one lumen suitable for delivery of a gelling material to a treatment space bounded by two or more of the uterine wall, the membranes, and the proximal cervix.

A method involving applying a fluent material to an amniotic membrane of a patient or a uterine wall of a pregnant patient, and causing the fluent material to become nonfluent.

A method involving applying any one of a synthetic fluent material and a polysaccharide to an amniotic membrane of a patient or a uterine wall or cervix of a pregnant patient, and causing the synthetic fluent material or polysaccharide to become nonfluent.

Other advantages, novel features, and objects of the invention will become apparent from the following detailed description of the invention when considered in conjunction with the accompanying drawing, which is schematic not intended to be drawn to scale.

DETAILED DESCRIPTION OF THE INVENTION

Figure 1:
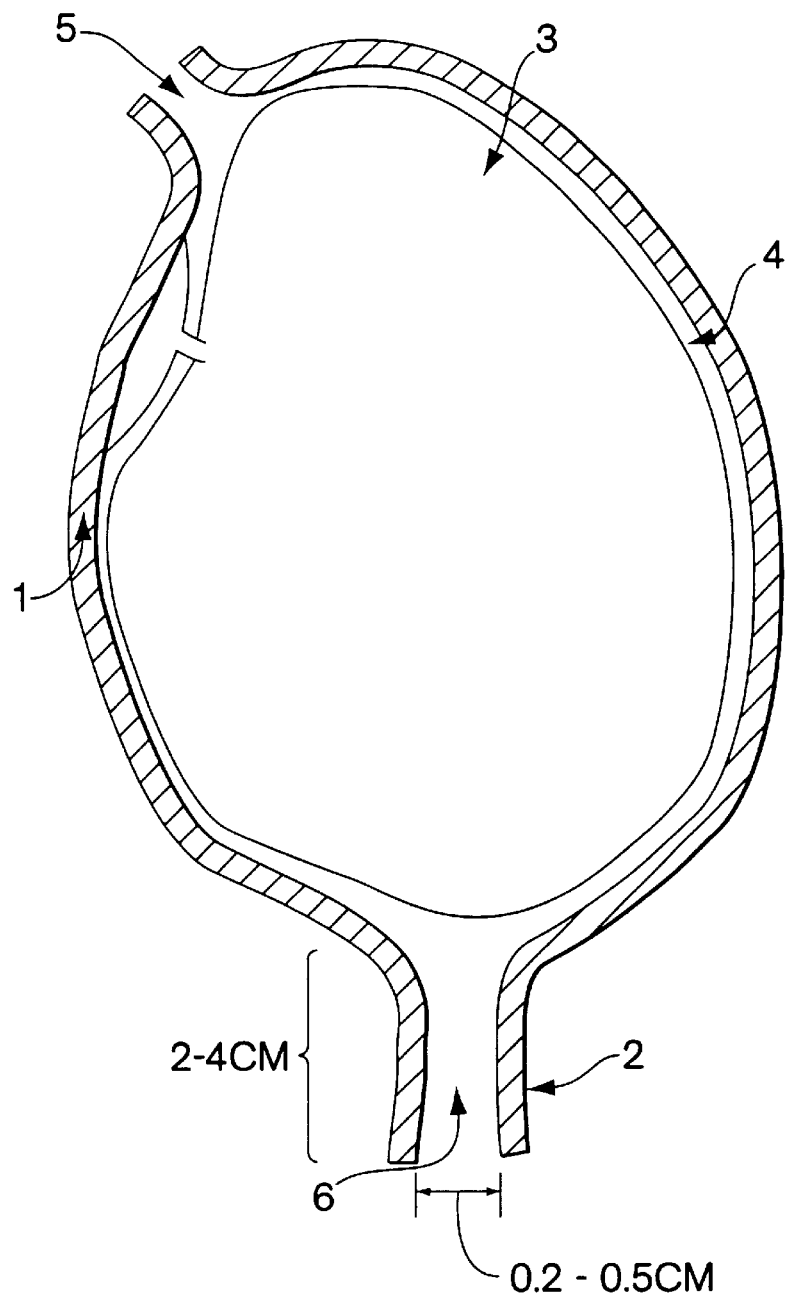
FIG. 1 is a schematic diagram of a gravid uterus for the purpose of illustrating techniques of the invention.

Definition: In this application, "the membranes of pregnancy" is meant to define the particular anatomy of the human membrane system which is formed to enclose a fetus. The term "chorioamniotic membrane" is sometimes used. In the description herein, and in the claims, the phrases "the membrane(s)" or "the amniotic membrane(s)" are intended as abbreviations of the terms "the membranes of pregnancy" or "chorioamniotic membrane".

The present invention, generally, provides techniques for treatment of PROM and other lesions, natural or surgical, which allow leakage of amniotic fluid before birth is desirable. A primary purpose of such treatment is to extend the period of pregnancy by the control of the leakage leakage of amniotic fluid out of the uterine cavity following PROM and to prevent the entry of infectious agents. The primary objective of such treatment is to prevent or minimize the leakage of amniotic fluid out of the uterine cavity. A related objective is to prevent or to minimize the invasion or proliferation of bacteria and other pathogens. This may be achieved by a combination of mechanical barrier to pathogen entry, or by administration of antibiotics and other therapeutic agents. Therapeutic agents may be administered locally, preferably in combination with the means for preventing efflux of amniotic fluid, or systemically, or both.

Prevention or minimization of fluid leakage, according to this invention, typically involves applying fluent material to physiology associated with pregnancy, and causing the material to become non fluent in situ. This is typically accomplished by delivering the fluent material to the site of the rupture, or to an area at which efflux of amniotic fluid may be blocked. The fluent material then becomes nonfluent at a selected site, which may be the actual site of the rupture of the membrane, through any conventional means. These include those known in the art, such as polymerization, crosslinking, gelling, precipitation, coacervation, phase separation and the like.

Another aspect of the invention provides a self sealing access route to the amniotic membrane to supplement amniotic fluid or to deliver drugs to the amniotic fluid or both.

Another aspect of the invention provides a sterile access route to treat the uterus, amniotic membrane or cervix of a pregnant patient.

Another aspect of the invention provides methods and materials for repair or resealing of an amniotic membrane puncture or incision made for diagnostic or surgical purposes.

The therapeutic objectives of the invention are achieved by creation of a seal which partially, essentially or completely seals a rupture (including a surgical rupture) of the membranes of pregnancy and controls efflux of amniotic fluid from the membranes; or by creation of a barrier which blocks efflux of amniotic fluid from the uterus, for example by blocking the cervix or other anatomical site; or by a combination of such methods.

Typically, elements of the preferred embodiment of the invention include a barrier-forming material, optionally in combination with a preformed or partially preformed barrier; apparatus or agents for creating a barrier from the precursor; if required; and instruments and techniques for application of the barrier-forming materials to the site. The barrier forming material preferably is a nonfluent material which on becoming nonfluent is useful for creating a seal. Optional elements of the invention include the incorporation of biologically active material in the barrier-forming, and the use of the barrier-forming materials as a route to supplement the amount of amniotic fluid in the uterus.

In order to diminish loss of amniotic fluid, an implant or sealant should provide a water-resistant seal at one or more points in the effluent pathway. One site which provides facile access in the pathway is the cervix, which has a lumenal diameter in the range of millimeters. When the cervix can be essentially completely sealed, or partially sealed, then the amniotic fluid will be contained in the uterus. This can allow for replenishment of the amniotic fluid.

An effective seal can be accomplished according to the invention by either or both of at least two processes. Effective seals are partial, essentially complete, or complete eals that allow the pregnancy to continue at least one week, preferably two weeks, most preferably three weeks or more. In a first process, the sealing materials can be made to tightly adhere to tissue surfaces of the proximal cervix and surrounding uterine tissues, and optionally to the membranes of pregnancy or to the cervical canal itself. Procedures are known which enhance the adherence of a sealing material to a tissue. These known methods include the process of "priming" of the tissue surface to enhance polymerization or other reaction of the barrier-forming material at the site. One example of such a process is described in U.S. Pat. No. 5,800,373. Another procedure for enhancing the adherence of a sealing material to tissue is the direct covalent reaction of the material with a tissue surface, as achieved for example by a cyanoacrylate glue. Benefits of such procedures include the fact that the seal can be formed and maintained independent of the posture of the mother; the seal can have a wide range of acceptable physical parameters; and the sealing plug or barrier can be relatively small. A disadvantage of such procedures includes the fact that degradation of the sealing material at the interface with the tissue, or natural turnover of the surface of the tissue, can allow undesired premature leakage.

Another method of implementing the above-described first process includes the provision of a flexible, conformable sheet of material, optionally having at least some degree of adherence to a tissue surface, against the proximal cervix and surrounding uterine tissue so as to block the opening of the cervix. The force is initially provided by the weight of the fetus and amniotic fluid. As pregnancy progresses maintenance of the seal will increasingly be independent of posture. An advantage of this method includes the lack of criticality of the interface between the implant and the uterine tissue; a disadvantage is the initial postural dependence and possible loss of seal. Because a large contact area is favorable for such a procedure, it is typically preferably accomplished by forming the sheet of material in place. Forming the sheet of material in place can be less difficult, and less dangerous, than attempting to insert a preformed sheet.

For some embodiments sealing materials form a flexible barrier preventing leakage of fluids. A flexible barrier as used here refers to a non-fluent material that is not rigid and is conformable. For embodiments involving the use of a flexible barrier, it is also typically desirable to employ a material which can swell to a defined extent upon contact with water and bodily fluids. When such material swells, it tends to occupy the space between the uterine wall and the membranes of pregnancy, thereby improving the seal, and allowing the seal to be maintained independent of the posture of the patient more quickly.

A combination of the above two methods for implementing the first process in a single implant is thus clearly preferable. A tightly conforming seal can be highly useful in the immediate aftermath of a medical procedure to correct PROM, while the pressing of a flexible material against the uterine wall can be preferable in later stages. As described in the examples below, it is possible to fabricate such an implant in place.

The second process is to directly seal the rupture in the membranes of pregnancy. It is not always possible to determine the location of the rupture accurately, but when the location can be determined, directly sealing the rupture can be preferable, because this technique can minimize the potential infiltration of pathogens into the amniotic fluid. The performance requirements for a membranes sealant to be used to directly seal a rupture in the membranes of pregnancy can be generally similar to those for the cervical sealants described above for use in the first process; however, for materials for use in the second process adherence to the tissue of the amniotic membrane is more critical. The use of sealants able to directly seal ruptures in membranes can be especially desirable when the membranes of pregnancy are being resealed after a surgical intervention or a diagnostic procedure.

For any of these approaches, the sealing material is preferably biocompatible and non-toxic to mother and fetus. In addition, in preferred embodiments no component of the sealing system can stimulate uterine contraction.

In one embodiment, one or more fluent materials are applied to one or more of the uterine wall, cervix and the membranes of pregnancy such as amniotic membrane of a patient and subsequently made non fluent. As used herein, "fluent" is meant to define a material having a viscosity low enough that the material can be moved through a lumen of a typical medical instrument of diameter of less than about 5 mm, preferably less than about 2 mm, and applied to a tissue surface near the distal end of the instrument and made to conform to the tissue surface. That is, it has viscosity low enough to flow onto a tissue surface and assume conformal contact with the tissue surface, or to be applied to the tissue surface and urged against the tissue surface and reconfigured to conform to the tissue surface, all at a physiologically compatible temperature in the range of about 4 deg. C to about 50 deg. C. "Non fluent" is meant to define a condition in which the fluent material has been solidified, or increased in viscosity, to the extent that it is self-supporting and does not flow, spontaneously, at a tissue surface at physiological temperature, i.e., in the range of about 30 to about 42 deg. C. Provided that the viscosity is low enough to permit administration, a higher viscosity within the acceptable range can often be desirable. More viscous fluent materials are typically more resistant to dilution with bodily fluids, such as amniotic fluid. Viscous fluids also tend to persist longer at the site of application, and are thus less likely to migrate away from the application site before becoming non-fluent. Thus, a preferred fluent sealing material could have a viscosity of at least 100 centipoise, more preferably at least several hundred centipoise, and most preferably in the range of about 1000 to 10,000 centipoise.

Fluent materials of the invention can be used to form partial or complete seals of lesions, ruptures, incisions (including surgical incisions), tears, and the like, of physiology associated with pregnancy. As used herein, "physiology associated with pregnancy" means membranes of pregnancy, or other portions of the reproductive system of a pregnant female, especially the uterine wall or cervix. "Seal" means partially, essentially or completely covering a hole, lesion, or other tissue surface that is beneficially treated by protection and/or isolation from a surrounding environment; joining or bridging portions of tissue that have become detached by tearing, surgical incision, rupture, or the like; or a combination. Seals can be partially, essentially complete or complete. As an example of partial sealing, a tear or incision might be partially sealed to the extent that healing is promoted and occurs spontaneously, or a rupture, hole, or other site that can involve leakage can be sealed to the extent that the rate of leakage is reduced to a physiologically acceptable level for a particular physiological condition. For example, in an instance of an unacceptable amniotic fluid leak, where a partial seal reduces the rate of leakage to the extent that amniotic fluid can be replaced interventionally (e.g., injection of saline), then the partial seal is effective therapeutically. Essentially complete seals are partial seals which reduce the rate of leakage to the extent that the amniotic fluid can be replaced naturally. In other cases, seals are complete, i.e., a tear, lesion, or surgical incision is covered or joined essentially completely, or a hole or other site of leakage is plugged or covered to the extent that an essentially fluid-tight seal is formed. In some cases, a seal may be formed according to the invention that both achieves the objective of isolation (i.e., containing fluid at a site of leakage) and creates a septum to facilitate future access from one side of the seal to the other through the seal. For example, when a hole in an amniotic membrane is sealed with material of the invention, proper selection of that material can create a septum through which needles or other interventional apparatus can be passed and removed without disturbing the fluid-tight nature of the seal. (Effective seals are partial, essentially complete or complete seals that allow the pregnancy to continue at least one week, preferably two weeks, or most preferably three or more weeks).

1. Fluent Materials; Tissue Adherence; Mechanical Properties a. Fluent Materials Any fluent material that is physiologically compatible and capable of becoming non fluent may be used. The fluent material can be selected from the class of natural polymers, synthetic polymers, polymerizable small molecules, tissue adhesives, gels and hydrogels. Properties of the non fluent material will be selected according to the use, using principles as known in the art.

As an example, a particular family of materials and techniques that has been developed for reliable sealing of leaking lesions in tissues are suitable for use as fluent materials of the invention. These materials and techniques have been used to treat release of air from injured lung, release of cerebrospinal fluid from injured dura, and blood leakage from anastomosed vessels. The materials can be made to adhere tightly to tissue surfaces and can be formulated from polymerizable materials for particular applications. These formulae can readily be adapted to use the improved system described herein with little experimentation. These materials and techniques are described in U.S. Pat. Nos. 5,410,016; 5,573,934; 5,800,373; 5,844,016 and 5,900,245 and in co-pending U.S. application Ser. Nos. 08/973,077 and 08/944,739 as well as in International Patent Publication Nos. WO 96/29370, WO 98/2243 and WO 99/07417. The disclosures of the above-identified patents and applications are incorporated by reference as part of the disclosure herein.

In the particular application of formation of mechanical barriers or sealants and other biologically related uses, the general requirements of the fluent materials are biocompatibility and lack of toxicity. For all biologically related uses, toxicity must be low or absent at all stages for internally applied materials and the fluent solutions should not contain harmful or toxic solvents. Biocompatibility, in the context of biologically related uses, is the absence of stimulation of a severe, long lived or escalating biological response to an implant, and is distinguished from a mild, transient inflammation which accompanies implantation of essentially all foreign objects into a living organism.

Where material of the invention is to be used to seal against the leakage of fluid, in particular amniotic fluid, the non fluent material must have sufficient tensile strength to support the hydrostatic pressure of the fluid, which will be up to 30 cm. of water at rest. To allow for activity, the non fluent material should withstand transient increased pressures, such as 150, 250, 380 and most preferably 500 cm of water.

It is preferable that the non fluent material adhere to tissue surfaces, be flexible, and have some elasticity, or repeatable strechability, thereby conforming to the shape changes which occur during the continuation of gestation, and in normal movement.

It is also preferable that the non fluent material be biodegradable, so that it does not have to be retrieved from the body. Biodegradability, in this context, is the predictable disintegration of an implant into small molecules which will be metabolized or excreted, under conditions normally present in the living tissue. However, because the materials of the invention will naturally be removed from the body at the time of birth, biodegradation of the implant is less important in treatment of PROM than in many other treatments.

Hydrogels are known materials that are a preferred fluent material for formation of a barrier material in the invention. Hydrogels have numerous properties favorable to their use in this application, which include excellent biocompatibility; low, controlled rates of water migration through a gel; controllable strength, elasticity, degree of swelling and gelatinization, and pre-gelation viscosity; and the ability to be cast in place to ensure conformal fitting to the available spaces. Suitable hydrogels may be either biodegradable or non-degradable; if degradable, their strength and other key properties should not change significantly for several weeks, preferably for one to two months, and more preferably for about four months or more.

Hydrogels suitable for the use of the invention, and methods for their formation, are known. A wide variety of hydrogels are known which may satisfy the above criteria. Hydrogels formed of natural gel-forming polysaccharide and protein polymers can serve a barrier function. These polymers are believed to be of low toxicity, and the polymerization to form a gel is in many cases spontaneous. Such polymers include, among others, agarose, alginate, pectin, xanthan, gellan, carrageenan, konjac glucomannan, galactomannans, chitosan, hyaluronic acid, collagen, and gelatin. These polymers typically are soluble under certain conditions, and form an insoluble gel on addition of certain ions, such as calcium, potassium or hydrogen, or upon cooling or warming, or a combination of these.

Both natural and synthetic ionic polymers can participate in precipitation, coagulation or coacervation reactions, in which the ionic groups of a polymer react with the ionic groups, typically of opposite charge, or with selected non-ionic groups, of another polymer. These reactions are a useful way of forming barriers from fluent materials.

Other gel-forming materials include synthetic polymers bearing reactive groups ("macromers"), which class includes natural polymers to which synthetic reactive groups have been grafted or otherwise covalently linked. Such polymers should have a molecular weight sufficient that they do not readily penetrate into cells, so that they are of low toxicity. Small polymerizable materials can be too toxic to be used as the primary polymer source, but may be used in polymerizing mixtures as a polymerization aid. In addition, the materials used in forming barriers or sealants should not induce uterine contractions. Such reactive polymers typically have the structure of a core polymer, with reactive groups appended to the core, or inserted into the backbone. Examples of such polymers are polysaccharides, polyamides, polyesters, polyorthoesters, polycarbonates, polyalkylene oxides, polylactones, poly (n-vinyl) compounds such as polyvinylpyrrolidone, poly(meth)acrylates (i.e., polyacrylates or polymethacrylates or a copolymer thereof), polyvinyl acetate and polyvinyl alcohol, polyanhydrides, silicones, and copolymers thereof.

Preferred reactive groups include free-radical-polymerizable groups, such as (meth)acryl, allyl, vinyl, fumaryl, maleyl and other ethylenically-unsaturated groups. These compounds have good storage stability, and their crosslinking to form gels can be controlled. Other reactive systems include spontaneously-reacting pairs of substituents, including, for example, isocyanates, succinimides, maleimides, tresylates and other electrophilic or leaving groups with nucleophilic groups such as amines, thiols or alcohols, or of epoxides with amines or alcohols. More generally, the exact composition of the barrier-forming material is not believed to be critical, and any reactive group may be suitable in the practice of the invention, The reacting groups must be in an appropriate stoichiometry to provide crosslinking. These ratios are well-known, and generally requires a substantial proportion of di-substituted and a significant proportion of tri- or higher substituted reactants. (Free-radical reactants generally require only di-substituted reactants).

A preferred material is a synthetic gel-forming material, having properties which can be tailored to the PROM repair application. One known example, described in U.S. Pat. No. 5,410,016, has a polyethylene glycol (polyethylene oxide; polyoxyethylene; PEG) core which has been covalently modified with a polymerizable group, such as an acrylate group. Such materials may also have a degradable linkage between the acrylate and the PEG. In such materials, the post-polymerization degree of elasticity and of swelling, and the prepolymerization viscosity, can be controlled by selection of the final polymer concentration, and the molecular weight of the PEG segment and its degree of dispersity. Such materials can readily be polymerized by photopolymerization in the presence of a photoinitiator, by chemical polymerization with suitable reagents, or by a combination.

Other polymeric materials are known, in addition to PEG-acrylates and their variants in which the acrylate group is replaced with a methacrylate, or a cinnamate group, which would be suitable for the invention. These include other materials described in U.S. Pat. Nos. 5,410,016 and 5,573,934, including acrylated derivatives of polysaccharides and of other synthetic polymers, with or without degradable groups. Other synthetic polymers are known which could be suitable for this application, including, for example, polymers described in U.S. Pat. No. 4,938,763 to Dunn, et al., U.S. Pat. Nos. 5,100,992 and 4,826,945 to Cohn et al, U.S. Pat. Nos. 4,741,872 and 5,160,745 to De Luca et al, U.S. Pat. No. 4,511,478 to Nowinski et al., U.S. Pat. No. 5,198,507 to Kohn et al., and U.S. Pat. No. 5,219,564 to Zalipsky et al., all incorporated herein by reference. Other polymers may be suitable for the application if they meet the basic requirements needed to practice the invention: safety, controllable polymerization, adequate tensile strength, conformance, biocompatibility, and non-toxicity.

Protein-based gel systems are also known, such as fibrin-based glues. Fibrin glues and related materials are less desirable for this application because of their lack of elasticity and long term adherence; their short but otherwise unpredictable lifetime due to proteolysis by natural enzymes of varying activity; and their potential allergenicity, infectivity and susceptibility to bacterial attack. Accordingly, in preferred embodiments they are excluded from use in the invention.

b. Gel Application and Polymerization

As noted, one aspect of the invention involves inserting at least one preformed plug or other barrier-creating device, for example comprising at least one of a biologically compatible polymer and a hydrogel, into the cervix of a patient to form a seal resistant to hydraulic pressure (a "hydraulic seal"). Simple blockage by placing or creating a gel plug in the cervix may be sufficient to retain amniotic fluid or slow its loss. To achieve this function, the gel must be conformal and preferably elastic having a low elastic modulus and being easily stretchable. It is advantageous if the gel that is formed adheres to the tissue, forming a bond or complete seal which does not permit passage of amniotic fluid. Even if the adherence to the cervix or the uterine wall is limited, an initial or partial seal will promote retention of fluid, and perhaps also promote healing of the amniotic membrane. A partial seal is also beneficial since it may slow the leak of amniotic fluid sufficiently to allow replenishment of the amniotic fluid. Adherence of a plug or other barrier to the amniotic membrane is desirable, as it will promote retention of the gel in its applied location, and may minimize further tearing of the membrane, and/or promote its healing.

Methods of forming photopolymerized gels with adherence to tissue surfaces are described in the above-cited U.S. application Ser. Nos. 08/973,077 and 08/944,739 and U.S. Pat. Nos. 5,800,373; 5,844,016 and 5,900,245. In brief, the tissue is primed with a fluent primer material containing a tissue-adherent dye which is active as a photoinitiator or photosensitizer, and also containing appropriate electron-transfer reagents such as amines. Optional primer ingredients include polymerizable monomers and components of "redox" polymerization systems, such as iron salts, reducing sugars or peroxides. Excess primer material is optionally removed, and then a fluent material such as a sealant prepolymer solution, also containing photoinitiation and optional redox components, is introduced. During or after the introduction of the sealant component, the system is photopolymerized, for example with visible or near UV light. The resulting gels are adherent to tissue, and also are sufficiently elastic to conform to tissue movements. These hydrogels also swell controllably in the presence of excess biological fluid, and can be biodegradable by spontaneously degrading to small metabolizable or excretable components under normal conditions in human or animal tissue with lifetimes ranging from weeks to a year. These materials are preferred in the invention.

However, it should be kept in mind that in the present invention, adherent barrier-forming compositions are not confined to those described above, but may be constructed of other adherent materials which can form barriers or seals in the relevant sites for control of PROM. In particular, materials which spontaneously react with themselves and with tissue, such as cyanoacrylates, leaving-group derivatized reactants, and the like, can be of use in forming a well-adhered barrier, alone or in combination with other materials. Adherence of a barrier, partially or completely pre-formed, may be achieved by use of known medical adhesives, such as acrylates and urethanes. Certain coacervating systems, such as chitosan or polyethyleneimine with polyanions, can adhere to tissue as well as form barriers retarding fluid flow. Moreover, the materials may be at least partially hydrophobic, having a low solubility in water, provided they are sufficiently fluent for administration to the tissue sites for sealing. Materials fulfilling some of the above criteria are described in U.S. Pat. Nos. 5,744,545, 5,614,587, and 5,874,500 to Rhee et al; U.S. Pat. No. 5,514,379 to Weissleder & Bogdanov; U.S. Pat. No. 5,173,301 to Itoh and Matsuda; Barrows et al, U.S. Pat. No. 5,583,114; Lipatova et al U.S. Pat. No. 4,057,535; Doi et al U.S. Pat. No. 4,839,345; Harris et al U.S. Pat. Nos. 5,252,714, 5,739,208 and U.S. Pat. No. 5,672,662; Matsuda et al U.S. Pat. Nos. 4,740,534, 4,994,542 and 4,806,614; English et al., U.S. Pat. No. 4,804,691; WO 99/03454 to Hubbell et al; and WO 99/14259 to Harris.

In any barrier or sealant system, for treating PROM, biologically active molecules which are useful to enhance the duration of the pregnancy and its management may be included in the gel-forming solution or other fluent material. These may include tocolytic agents which inhibit uterine contractions; antibiotics; bacteriostatic agents; contrast agents for sonography, radiography, or MRI, for example; growth factors for promoting healing of the membranes; hemostatic agents and the like. The materials included must be selected for non-toxicity to the fetus and the mother.

Many hydrogels are substantially self sealing, in that if punctured, for example with a needle, they will re-close sufficiently on removal of the needle to prevent significant fluid leakage. Gels which swell in water often exhibit this property. Non fluent materials with this property, including the preferred gels described above, will define septa that allow replenishment or exchange of amniotic fluid via a needle or catheter during the remainder of the pregnancy if required and will also allow introduction of therapeutic agents such as antibiotics directly to the amniotic fluid as needed.

Pre-formed gels, optionally dehydrated or partially dehydrated, could also be used in the procedure. Particularly in an emergency situation, a rapidly-swelling gel could provide temporary blockage to slow loss of amniotic fluid. However, the insertion of such a pre-form has the potential to trigger uterine contractions and labor, and a pre-formed gel can be mis-positioned. Pre-forms are thus less preferred when the opportunity to form a gel in situ is available.

2. Methods and Devices

The placement of the materials of the invention is best understood by reference to FIG. 1. The essential elements of the anatomical situation are the uterine wall 1, the cervix 2, the amniotic membrane 3 enclosing the fetus, the abdominal wall 4, and a possible transabdominal access route 5. The cervical canal diameter width is not shown to scale, being actually in the range of a few millimeters unless dilated.

There are two principal routes by which material of the invention could be placed in the uterus, especially near the proximal cervix: a trans-vaginal route, and a trans-abdominal route. These are discussed in turn.

a) Transvaginal. One route of placement of material is via the vagina and the cervical canal. Because the patient has leaked some amniotic fluid due to the rupture, positioning of the patient so that the cervix is raised above the uterus, for example, the Trendelenburg position, will tend to create space in the uterus near the proximal cervix (,i.e., the portion of the cervix attached to the uterus). The non fluent material is then administered to the space within the proximal cervix and between the amniotic membrane and the local uterine wall. The extent of penetration of the non fluent material between the amniotic membrane and the wall, at the periphery area bounded by the amniotic membrane, the proximal cervix and the uterine wall, would depend on the injection pressure which could be applied, and on the patient's position and degree of loss of amniotic fluid, each of which would influence the local hydrostatic pressure on the amniotic membrane.

Mechanical considerations in device selection or design include the narrow diameter of the cervical opening at the stage of pregnancy at which PROM occurs, which is typically 3 to 5 mm. Larger devices can stimulate uterine contractions, which could lead to premature labor.

In the simplest embodiment, a preformed gel can be applied to the cervical area without a specialized device. However, the degree of penetration would be unpredictable. Other simple applicators include a syringae, optimally in combination with a needle. Again, control is not precise. More complex application systems are preferable, especially for the preferred resilient, highly-adherent photopolymerized gels. A well-controlled system is particularly important to ensure that the formed gel is significantly larger, within the treatment space, than the cervical opening, With the preferred polymers of the invention, the application device must provide at least one conduit for the injection of a fluent material. Optional but preferred ancillary functions of the application device comprise any of the following:

a source of electromagnetic radiation or other activator of polymerization;

a second lumen or channel for injection of primers (if it is desired to administer primer separately) or co-reactant;

an optional mixing chamber or mixing nozzle for mixing primer or co-reactant and gelling material;

a channel for removal of excess primer or other applied fluid by vacuum or flushing, which may be the same as one of the application channels;

an endoscope or hysteroscope or other visualization device; and markers to allow verification of the instrument's position, for example by ultrasound.

The device may also comprise one or more inflatable balloons or mechanical occlusion devices, or a swellable device, or other means for temporary occlusion of the cervix. This will prevent backflow of applied materials and/or will stop amniotic fluid efflux during formation of the gel barrier. Devices such as those described in International Patent Application Serial No. PCT/US96/03834 (Publication WO 96/29370) can be modified as necessary to incorporate features described above. Balloons for occlusion, etc. are known, as described for example in International Patent Publication WO 90/01969.

In cervical applications, a useful accessory is a sleeve, which can be inserted through the vagina and into the distal cervix to facilitate placement of other instruments, and to minimize both contamination of the field and trauma to the cervical canal. The sleeve may be as simple as a disposable length of tubing, of appropriate diameter, and optionally somewhat flexible for minimal trauma in placement.

b). Transabdominal. A second route of administration is transabdominal. Endoscopic and laparoscopic procedures and devices, and other sterile surgical procedures, are well known. In particular, the transabdominal route is often used to take samples for amniocentesis in which a needle, or other instrument, is inserted through the abdominal wall and through the amniotic membrane into the amniotic fluid for sampling. A similar entry procedure may be used to form a non fluent material at any site on membranes of pregnancy such as within the uterus. In particular, the transabdominal route may be preferred for the formation of a non fluent material in the cervix. Although the need to create an incision is a disadvantage, the non fluent material will be formed in a sterile manner, without the risk of introducing additional contamination in passage through the vagina and cervix.

For example, an access site is selected and is opened through the abdominal wall and through the wall of the uterus. Conventional means for such opening, such as with a trochar and obturator, can be used. Ultrasonic or other guidance will be used to prevent penetration of the membranes. Next, a penetration instrument with a tip suitable for blunt dissection is inserted between the membranes and the uterine wall. Under guidance as required, the instrument is then used to form a passage between the membranes and the uterus extending to the region of the proximal cervix, or to the area of the rupture of the membranes, if known, thereby allowing percutaneous access to the treatment space.

The penetration device may or may not contain the other components described for the transvaginal treatment instrument. For simplicity, the penetration device will not contain the other components, but may carry a releasable sheath. After constructing the passage, the sheath remains in place to provide a sterile low-friction, low-trauma passage for the application instrument. Alternatively, the dispensing instrument and the penetration instrument may be combined.

After passage to the treatment space, the application instrument operates in essentially the same manner as the transvaginal applicator, and has the same set of options in terms of mechanisms of application and of visualization. In addition, visualization or light delivery or both could be provided transvaginally.

In addition, a device for displacing fluid present at the application site, such as amniotic fluid, can be useful in achieving proper consistency of the sealing or barrier-forming material, or its adherence to the local tissue. For example, a "caisson' could be formed by a flexible balloon, optionally biodegradable, which could then be filled with the fluent barrier-forming material.

For example, the patient can be placed in the appropriate position, and the volume of the treatment space is then estimated from ultrasound measurements. Then, as an option for some polymerizable systems, a similar volume of a priming solution is injected through a first lumen in the instrument, to stain the walls of the treatment space with an initiator or catalyst of polymerization and other polymerization aids, or in general a material designed to increase adherence of the barrier to the tissue may be used. Excess initiator or other solution is removed by application of mild suction to the primer lumen. Then a polymerizable gel-forming solution, of about the estimated treatment space volume or with a small excess, is injected through a lumen, which may be the primer lumen or a different lumen. A gel-forming macromer is synthesized according to methods known in the art, for example U.S. Pat. No. 5,410,016 or any of the other cited applications. The gel-forming solution should preferably be of high viscosity, or even of a paste-like consistency when in the body, to prevent unwanted spreading of the agent beyond the treatment space.

The macromer is then allowed or caused to polymerize. For example, the polymers of U.S. Pat. No. 5,410,016 may be photopolymerized. Electromagnetic radiation such as light may be applied via a lumen of the application instrument, for example via a fiber optic light guide equipped with a suitable diffuser. Alternatively, or in addition, a light source, such as an optical fiber, is positioned transvaginally to within about a millimeter from the proximal end of the cervix. Light, which is matched in wavelength to the initiators used (such as blue to green with preferred initiators such as eosin), is then applied to crosslink the gel. After crosslinking of the gel, the instrument or instruments are withdrawn and the incision is repaired.

Any other convenient method of polymerization, gelation, precipitation, or the like may be used to form a barrier, or to adhere a barrier to a tissue surface.

Other Transabdominal Uses:

For use in sealing leaks caused by medical procedures, such as amniocentesis or laparoscopic fetal surgery, where the location and size of the lesion are known, it may be sufficient to form a tissue-adherent gel patch on the access site in the membrane. This route would be especially effective to seal the amniotic membrane after amniotic fluid sampling or other procedures which compromise amniotic integrity, such as fetal surgery. It might be desirable to use a blunt dissector to create a small treatment space adjacent to the site, between the membrane and the uterine wall, to ensure retention of the gel at the site.

Moreover, with ultrasonic or endoscopic guidance, an instrument could be positioned to deliver fluid between the amniotic membrane and the uterine wall at a location away from the cervix. The fluid could be any of replacement amniotic fluid, materials for treatment (such as drugs), and prepolymers for forming a gel.

In addition, the methods of the invention can be used to simplify fetal surgery. This is now performed endoscopically, with great difficulty. The methods of the invention can seal the small incisions necessary for such surgery, as noted above. They also allow surgical opening of the membranes, as for example in a caesarian section, to allow open surgery to be performed on the fetus. Such surgery can then be followed by resealing of the membranes, replenishment of the amniotic fluid, and closure of the uterine wall and abdominal wall. Such an operation is not possible without the ability to reliably repair a rupture of the membranes to provide a fluid tight seal.

An optional addition to any of the fluids used to form barriers or seals is a means for ultrasonic visualization of the fluid. This may be as simple as the deliberate introduction of bubbles, if the fluid is highly viscous. Otherwise, any of the known additives for improving acoustic contrast are suitable, such as air-filled vesicles, provided they are approved for use in pregnancy and are not inductive of contractions.

EXAMPLE 1

Application of Sealing System to Model Tissue

A model of a gravid uterus was constructed from a small pig bladder. The stub of the urethra was used to model the cervix, and the opposite end of the bladder was pushed in to form a cup-shaped construct. A purse-string suture was sewn into the rim, and then was tightened to maintain the configuration. In this geometry, the inverted bladder opposite the urethra simulated the membranes of pregnancy, and a small conical space was present at the end of the cervix, as it is in a human pregnancy.

A sealing system was formulated essentially as described in U.S. Pat. No. 5,944,016. A primer solution was made, containing about 30% wt/vol of a macromer, about 500 ppm eosin, and about 0.5% t-butyl hydroperoxide, in an aqueous buffer comprising about 90 mM triethylamine adjusted to about pH 7.0. The macromer had a core of polyethylene glycol (PEG), with a nominal (manufacturer's stated) molecular weight of 3500 Daltons. The PEG was extended at each end with about 2.5 lactide residues, and terminated with acrylic acid esters. Macromer synthesis is described in more detail in U.S. Pat. No. 5,400,016.

A sealing solution comprised an aqueous solution of about 20% of a sealant macromer. The sealant macromer comprised PEG of about 35,000 daltons, partially concatenated with trimethylene carbonate residues as described in WO 98/12243 or U.S. Pat. No. 5,900,245, and extended with about 5 trimethylene carbonate residues and capped with acrylic acid. The sealant also contained about 2% ferrous gluconate and about 5% fructose, all by weight, as well as about 50 ppm eosin and 90 mM triethylamine, pH 7.

Primer solution B about 2 ml B was injected into a bladder model, which was held with the urethra up to emulate the Reverse Trendelenburg position. After about a minute, excess primer solution was drained from the model. Next, about 4 ml of sealant solution was injected into the model. Then a fiber optic probe was inserted, and the model was held with the urethra up. Light (450–55-nm band pass filter; about 100 mW per square centimeter at 2 cm. from the tip) was applied to polymerize the primer and sealant. On dissection, it was found that a firm gel, tightly adherent to both bladder walls, had been formed between the bladder layers out to a distance of several centimeters. A thicker, somewhat plug-like region was formed near the urethra's entrance.

This model demonstrates application of the invention, and is suitable for routine experimentation to determine whether a particular polymer system is effective in forming a barrier which can be used to seal a uterus against loss of amniotic fluid.

This system can readily be adapted to a non-photocured system. For example, a mixture of electrophilically-reactive polymers and nucleophilically active polymers could be formed, by methods described in WO 99/14259, or U.S. Pat. Nos. 5,874,500 or 5,752,974, and rapidly injected while polymerization of the mixture is ongoing. The applicator tube would be coated so that the reacting mixture would not adhere to it, for example with polytetrafluoroethylene. Hydrophobic polymers could also be used, as in, for example, WO 99/03454.

Those skilled in the art would readily appreciate that all parameters listed herein are meant to be exemplary and that actual parameters will depend upon the specific application for which the methods and apparatus of the present invention are used. It is, therefore, to be understood that the foregoing embodiments are presented by way of example only and that, within the scope of the appended claims and equivalents thereto, the invention may be practiced otherwise than as specifically described. Modifications and variations of the present invention will be apparent to those skilled in the art. Such modifications are intended to come within the scope of the appended claims.

What is claimed is:

1. A method for treatment of premature rupture of the membranes of pregnancy (PROM), the method comprising the steps of:

applying a fluent material to a tissue selected from at least one of an amniotic membrane, a cervix, and a uterine wall; and causing the fluent material to become a non-fluent material that forms an essentially complete seal which retains amniotic fluid.

2. A method as in claim 1, wherein in the causing step the fluent material becomes non-fluent and forms a seal at the membrane or uterine wall, the causing being induced by one or more processes selected from at least one of a change in temperature, photoinitiation of crosslinking, chemical induction of crosslinking, spontaneous covalent crosslinking, ionic crosslinking, change in ionic strength or composition, change in pH, coacervation, and precipitation induced by change in solvent polarity.

3. A method as in claim 1, wherein the fluent material is biocompatible and non-toxic.

4. A method as in claim 1, wherein the non-fluent material forming the hydraulic seal has sufficient tensile strength to withstand a pressure of about 30cm. of water without mechanical failure.

5. The method of claim 1, wherein the non-fluent material forming the hydraulic seal has sufficient adherence to the adjacent tissues to withstand a pressure of about 30 cm. of water without substantial loss of adherence.

6. The method of claim 1, wherein the non-fluent material comprises a hydrogel.

7. The method of claim 6, wherein the hydrogel is formed from the fluent material by gelatinization or crosslinking.

8. The method of claim 1, further comprising applying a material to the tissue which increases the adherence of the seal to the tissue.

9. The method of claim 1, wherein the fluent material includes a therapeutic agent.

10. The method of claim 1 wherein the seal is at least partially on the fetal side of the amniotic membrane.

11. The method of claim 1, wherein the site of application to the tissue is approached by a route selected from a transvaginal route and a percutaneous route.

12. The method of claim 11, wherein the percutaneous route is transabdominal.

13. The method of claim 1 further comprising inserting an at least partially preformed barrier or sealant material.

14. A method comprising the steps of:
accessing at least one of the cervix, uterine wall, and amniotic membrane;
applying a fluent material to at least one of the cervix, uterine wall, and amniotic membrane; and
causing the fluent material to become non-fluent.

15. A method as in claim 14, the step of accessing involving:
inserting an endoscopic instrument percutaneously into a patient; and
bringing the endoscopic instrument into close proximity with at least one of the cervix, uterine wall, and amniotic membrane.

16. A method comprising:
introducing a treatment device into a vagina of a patient;
applying at least one of a synthetic fluent material and synthetic fluent hydrogel to at least one of a cervix, uterine wall and amniotic membrane; and
causing at least one of the synthetic fluent material and synthetic fluent hydrogel to become non fluent to form a seal.

17. A method comprising the steps of:
inserting at least one of a preformed plug into a cervix of a patient, wherein said preformed plug comprises at least one biologically compatible polymer; and
applying a fluent material into the cervix of a patient to form a seal.

18. The method of claim 17, further comprising applying a fluent material to at least one of the plug, a cervix, a uterine wall and an amniotic membrane, which increases the adherence of at least one of the plug and to at least one of the cervix, uterine wall and amniotic membrane.

19. The method as in claim 1 comprising:
sealing a surgical incision in at least one of an amniotic membrane and uterine wall of a pregnant patient by delivering a fluent material to the surgical incision and causing the fluent material to become non fluent to form a seal.

20. A method comprising the steps of:
inserting at least one of a sheath and tube into a vagina of a patient;
placing a treatment device in at least one of the sheath and tube; and
applying a fluent material into the vagina of a patient.

21. A method comprising:
accessing a treatment site of a uterine wall, amniotic membrane, or cervix of a patient percutaneously; and
therapeutically treating the treatment site.

22. A method for treatment of premature rupture of the membranes of pregnancy (PROM), the method comprising:
instilling a gelling material to form a layer in a treatment space, wherein the treatment space is bounded by one or more of the amniotic membrane, the cervix and the uterine wall; and
causing the material to form a hydrogel, thereby providing a hydraulic seal which retains amniotic fluid.

23. The method of claim 22, in which the gelation is induced by one or more of thermal gelation, photoinitiated crosslinking, chemically induced crosslinking, ionic crosslinking, and precipitation induced by change in solvent polarity.

24. The method of claim 22, wherein the gelling material is one or more of a natural material, including agarose, alginate, pectin, xanthan, gellan, carrageenan, konjac glucomannan, hyaluronic acid, collagen, and gelatin; and a synthetic material comprising a polymeric backbone bearing reactive groups.

25. The method of claim 24, wherein the backbone is selected from polysaccharides, polyamides, polyesters, polyorthoesters, polycarbonates, polyalkylene oxides, polylactones, poly (n-vinyl) compounds such as polyvinylpyrrolidone, poly(meth)acrylates (i.e., polyacrylates or polymethacrylates or a copolymer thereof), polyvinyl acetate and polyvinyl alcohol, polyanhydrides, silicones, and copolymers thereof.

26. The method of claim 24, wherein the reactive group is selected from free-radical-polymerizable groups, such as (meth)acryl, allyl, vinyl, fumaryl, maleyl and other ethylenically-unsaturated groups; urethane-forming pairs (isocyanates with amines); and epoxides with amines or alcohols.

27. The method of claim 22, further comprising the instillation into the treatment space of a material which increases the adherence of the gel to the tissues defining the treatment space.

28. The method of claim 22, wherein the instilled gelling material further comprises a therapeutic agent.

29. The method of claim 28 wherein the therapeutic agent is selected from tocolytics, antibiotics, bacteriostats, contrast agents for sonography, radiography, or MRI, growth factors for promoting healing of the membranes, and hemostatic agents.

30. The method of claim 22, wherein the route of instillation is transvaginal or transabdominal.

31. A device for treatment of PROM, wherein the device comprises a proximal end for manipulation of the device, a distal end for insertion into the patient's body, and at least one lumen suitable for delivery of a gelling material to a treatment space bounded by two or more of the uterine wall, the membranes, and the proximal cervix.

32. A method comprising:
  applying a fluent material to an amniotic membrane of a patient or a uterine wall of a pregnant patient; and
  causing the fluent material to become nonfluent.

33. The method as in claim 32, comprising causing the fluent material to become nonfluent and to form a seal at the membrane or uterine wall.

34. The method of claim 33, wherein the fluent material is applied to the amniotic membrane and at least one of a uterine wall and a cervix.

35. The method of claim 33, wherein the seal is a partial seal.

36. The method of claim 33, wherein the seal is an essentially complete seal.

37. The method of claim 33, wherein the seal is a complete seal.

38. A method comprising:
  applying any one of a synthetic fluent material and a polysaccharide to an amniotic membrane of a patient or a uterine wall or cervix of a pregnant patient; and
  causing the synthetic fluent material or polysaccharide to become nonfluent.

* * * * *

UNITED STATES PATENT AND TRADEMARK OFFICE
CERTIFICATE OF CORRECTION

PATENT NO.    : 6,350,463 B2  
DATED         : February 26, 2002  
INVENTOR(S)   : Stephen J. Herman et al.

It is certified that error appears in the above-identified patent and that said Letters Patent is hereby corrected as shown below:

<u>Column 18,</u>
Line 49, "malcyl" should be -- maleyl --

Signed and Sealed this

Fifteenth Day of October, 2002

*Attest:*

*Attesting Officer*

JAMES E. ROGAN
*Director of the United States Patent and Trademark Office*